(12) United States Patent
Ferro et al.

(10) Patent No.: US 9,782,429 B2
(45) Date of Patent: Oct. 10, 2017

(54) FORMULATION HAVING MOBILIZING ACTIVITY

(71) Applicant: GENTIUM SPA, Villa Guardia, Como (IT)

(72) Inventors: Laura Ferro, Milan (IT); Roberto Porta, Cernobbio (IT); Massimo Iacobelli, Milan (IT); Alessandro Massimo Gianni, Milan (IT); Carmelo Carlo Stella, Milan (IT)

(73) Assignee: GENTIUM S.R.L., Villa Guardia (IT)

( * ) Notice: Subject to any disclaimer, the term of this patent is extended or adjusted under 35 U.S.C. 154(b) by 449 days.

(21) Appl. No.: 14/323,918

(22) Filed: Jul. 3, 2014

(65) Prior Publication Data

US 2014/0363394 A1    Dec. 11, 2014

Related U.S. Application Data

(63) Continuation of application No. 12/755,321, filed on Apr. 6, 2010, now Pat. No. 8,771,663, which is a continuation-in-part of application No. 10/432,741, filed as application No. PCT/EP01/04105 on Apr. 10, 2001, now abandoned.

(30) Foreign Application Priority Data

Apr. 18, 2000  (EP) ..................... 00830293

(51) Int. Cl.

| A61K 39/395 | (2006.01) |
| A61K 31/7088 | (2006.01) |
| A61K 31/711 | (2006.01) |
| A61K 38/19 | (2006.01) |
| A61K 38/18 | (2006.01) |
| A61K 38/20 | (2006.01) |

(52) U.S. Cl.
CPC ........ *A61K 31/7088* (2013.01); *A61K 31/711* (2013.01); *A61K 38/18* (2013.01); *A61K 38/193* (2013.01); *A61K 38/2053* (2013.01)

(58) Field of Classification Search
None
See application file for complete search history.

(56) References Cited

U.S. PATENT DOCUMENTS

| 3,770,720 | A | 11/1973 | Bertellini et al. |
| 3,829,567 | A | 8/1974 | Butti et al. |
| 5,199,942 | A | 4/1993 | Gillis |
| 5,223,609 | A | 6/1993 | Fedeli et al. |
| 5,856,444 | A | 1/1999 | Kawakita et al. |
| 5,977,083 | A | 11/1999 | Burcoglu |
| 6,573,372 | B2 | 6/2003 | McCall et al. |
| 2004/0131588 | A1 | 7/2004 | Ferro et al. |

FOREIGN PATENT DOCUMENTS

| EP | 0 317 766 A | 5/1989 |
| EP | 0 416 678 A | 3/1991 |
| EP | 1 147 777 A1 | 10/2001 |
| EP | 0 937 461 B1 | 7/2005 |
| JP | 2149527 A | 6/1990 |
| JP | 8127539 A | 5/1996 |
| WO | WO 92 21402 A1 | 12/1992 |
| WO | WO 99 26639 A | 6/1999 |

OTHER PUBLICATIONS

Carlo-Stella, et al.; "Defibrotide significantly enhances peripheral blood progenitor cell mobilization induced by recombinant human granulocyte colony-stimulating factor"; Blood; vol. 96, No. 11 part 1, pp. 553A (Nov. 16, 2000).
Craddock, et al.; "Antibodies to VLA4 Mobilize Long-Term Repopulating Cells and Augment Cytokine-Induced Mobilization in Primates and Mic"; Blood; vol. 90, pp. 4779-4788 (1997).
International Search Report of International Application No. PCT/EP01/04105 with a mailing date of Oct. 23, 2001.
Kaushansky, et al.; "Hermatopoietic Growth Factors: Understanding Functional Diversity in Structural Terms"; Blood; vol. 82, No. 11, pp. 3229-3240 (Dec. 1, 1993).
Kojima, et al.; "Enhancement of Plasminogen Activator Activity in Cultured Endothelial Cells by Granulocyte Colony-Stimulating Factor"; Journal of Cellular Physiology; vol. 138, pp. 192-196 (1989).
Prosper, et al.; "Mobilization and Homing of Peripheral Blood Progenitors is Related to Reversible Downregulation of $\alpha 4\beta 1$ Integrin Expression and Function"; Mechanism of Trafficking of Peripheral Blood Progenitor; vol. 101, No. 11, pp. 2456-2467 (Jun. 1998).
PureLink brochure, Nucleic acid purification, Invitrogen, pp. 1-8 (2007).
Vermeulen, et al.; "Role of Adhesion Molecules in the Homing and Mobilization of Murine Hematopoietic Stem and Progenitor Cells"; Blood; vol. 92, No. 3, pp. 894-900 (Aug. 1, 1998).

*Primary Examiner* — Yunsoo Kim
(74) *Attorney, Agent, or Firm* — Perkins Coie LLP; Viola T. Kung

(57) ABSTRACT

The present innovation relates to a novel formulation capable of increasing the amount of stem cells and progenitor cells in circulation in the peripheral blood of a mammal; the formulation is characterized in that it contains defibrotide in combination with at least one haematopoietic factor having the capacity to mobilize haematopoietic progenitors, preferably G-CSF. In one embodiment, the formulation includes two separately administrable formulations, one containing a haematopoietic factor having the capacity to mobilize haematopoietic progenitors and the other containing defibrotide. The formulation is effective to achieve an increase in the number of haematopoietic progenitor cells that is greater than an increase in the number of haematopoietic progenitor cells achieved by the haematopoietic factor alone.

16 Claims, 6 Drawing Sheets

FORMULATION HAVING MOBILIZING ACTIVITY

This application is a continuation of U.S. patent application Ser. No. 12/755,321, filed Apr. 6, 2010, now U.S. Pat. No. 8,771,663; which is a continuation-in-part Application of U.S. patent application Ser. No. 10/432,741, filed Dec. 29, 2003, which is the National Stage Entry of PCT/EP01/04105, filed Apr. 10, 2001, which claims priority to EP 00830293.7, filed Apr. 18, 2000, the contents of the above-identified applications are incorporated by reference herein.

RELATED APPLICATIONS

This application is related to U.S. Pat. No. 4,985,552 and U.S. Pat. No. 5,223,609, the contents of which are expressly incorporated by reference herein.

BACKGROUND

The possibility of obtaining an increased amount of stem cells and haematopoietic progenitors in circulation in the peripheral blood of a mammal, and in particular in that of a human being, has for years been the subject of intensive research activity, the availability of stem cells and/or haematopoietic progenitors is in fact particularly important in sectors such as the autologous transplantation of circulating haematopoietic progenitors, the allotransplantation of circulating haematopoietic progenitors and in program for the gene therapy of circulating haematopoietic cells.

Although, after birth, stem cells and progenitor cells are located almost exclusively in the bone marrow, they nevertheless exhibit migratory properties; that is to say, under physiological conditions, they migrate through the cavities of the bone marrow and pass into circulation. That process, commonly known as "mobilization", can be amplified in mammals by various treatments, such as, for example, the administration of cytokines and, in particular, the growth factor of granulocyte colonies (G-CSF); the reverse process, known as "homing", occurs, for example, in irradiated receivers after the transplantation of haematopoietic cells; the mechanisms on which mobilisation and homing are based are, however, still obscure (C. F. Craddock et al., "Antibodies to VLA4 Integrin Mobilize Long-Term Repopulating Cells and Augment Cytokine-Induced Mobilization in Primates and Mice", Blood, Vol. 90, n. 12, 1997, pp. 4779-4788; F. Prosper et al., "Mobilization and Homing of Peripheral Blood Progenitors is Related to Reversible Downregulation of o.4151 Integrin Expression and Function", J. Clin. Invest., Vol. 101, n. 11, 1998, pp. 2456-2467; M. Vermeulen et al., "Role of Adhesion Molecules in the Homing and Mobilization of Murine Hematopoietic Stem and Progenitor Cells", Blood, Vol. 92, n.3, 1998, pp. 894-900).

DETAILED DESCRIPTION

Figure 1:
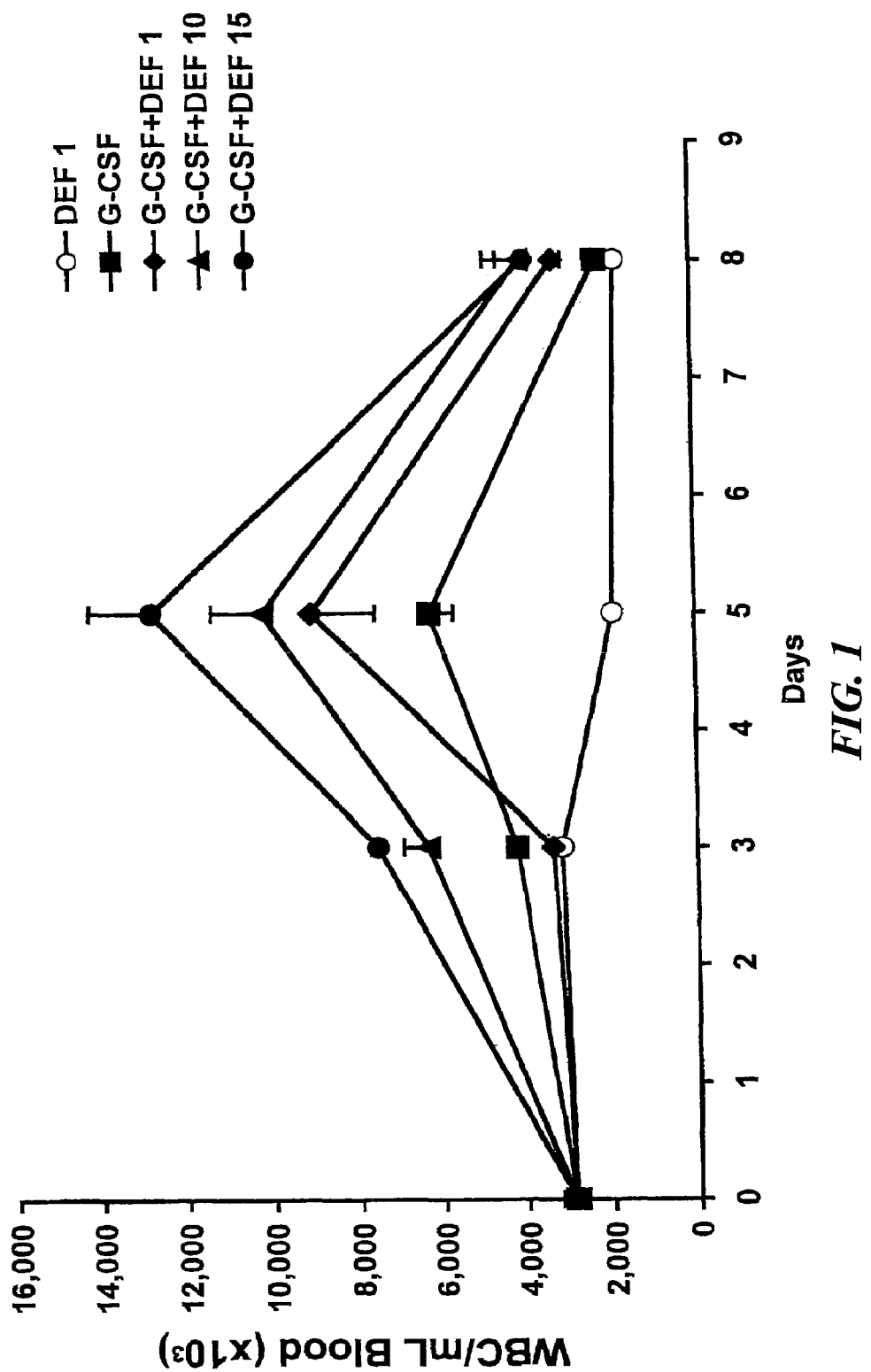
FIG. 1 shows the results of the effect of administration of G-CSF and/or defibrotide (DEF) on the amount of white blood cells (WBC) present in murine blood over days.

G-CSF (CAS registry number 143011-2-7/Merck Index, 1996, page 4558) is a haematopoietic growth factor which is indispensable in the proliferation and differentiation of the progenitor cells of granulocytes; it is a 18-22 kDa glycoprotein normally produced in response to specific stimulation by a variety of cells, including monocytes, fibroblasts and endothelial cells. The term defibrotide (CM registry number 83712-60-1) normally identifies a polydeoxyribonucleotide obtained by extraction (U.S. Pat. Nos. 3,770,720 and 3,899,481) from animal and/or vegetable tissue; this polydeoxyribonucleotide is normally used in the form of a salt of an alkali metal, generally sodium. Defibrotide is used principally for its anti-thrombotic activity (U.S. Pat. No. 3,829,567) although it may be used in different applications, such as, for example, the treatment of acute renal insufficiency (U.S. Pat. No. 4,694,134) and the treatment of acute myocardial ischaemia (U.S. Pat. No. 4,693,995). U.S. Pat. No. 4,985,552 and U.S. Pat. No. 5,223,609, finally, describe a process for the production of defibrotide which enables a product to be obtained which has constant and well defined physico-chemical characteristics and is also free from any undesired side-effects.

For the purposes of the present disclosure, the term defibrotide can be understood as meaning any oligonucleotide and/or polynucleotide obtained by extraction from animal and/or vegetable tissue, in particular from the organs of mammals. Preferably, defibrotide is produced in accordance with the methods described in the patents listed above which should thus be regarded as an integral part of the present description; even more preferably, it is produced in accordance with the method described in U.S. Pat. No. 4,985,552 and U.S. Pat. No. 5,223,609, which are incorporated by reference herein.

The present invention relates to a novel formulation capable of increasing the amount of stem cells and progenitor cells in circulation in the peripheral blood of a mammal; the formulation is characterized in that it contains defibrotide in combination with at least one haematopoietic factor having the capacity to mobilize haematopoietic progenitors, preferably G-CSF. In one embodiment, the formulation includes two separately administrable formulations, one containing a haematopoietic factor having the capacity to mobilize haematopoietic progenitors and the other containing defibrotide. The formulation is effective to achieve an increase in the number of haematopoietic progenitor cells that is greater than an increase in the number of haematopoietic progenitor cells achieved by the haematopoietic factor alone; in one embodiment, the defibrotide corresponds to a following formula of random sequence:

$P_{1-5}(dAp)_{12-24}(dGp)_{10-20}(dTp)_{13-26}(dCp)_{10-20}$ wherein P=phosphoric radical
dAp=deoxyadenylic monomer
dGp=deoxyguanylic monomer
dTp=deoxythymidylic monomer
dCp=deoxycytidylic monomer In one embodiment, the defibrotide has the following chemical-physical properties:
electrophoresis=homogeneous anodic mobility;
extinction coefficient, $E_{1cm}^{1\%}$ at 260+−1 nm=220°+−10°;
extinction ratio $E_{230}E/_{260}$=0.45+−0.04;
coefficient of molar extinction (referred to phosphorus), $\epsilon(P)$=7.750+−500;
rotary power $[\alpha]_D^{20°}$=53°+−6;
reversible hyperchromicity, indicated as % in native DNA, h=15+−5.

It has now surprisingly been found that it is possible to obtain increased mobilisation of stem cells and haematopoietic progenitors by the administration of defibrotide in combination and/or in close, temporal proximity with a haematopoietic factor having the capacity to mobilise haematopoietic progenitors.

As will be appreciated from the Examples, the administration of defibrotide in combination and/or in close temporal proximity with a haematopoietic factor having the capacity to mobilise haematopoietic progenitors permits the attainment of mobilisation levels much higher than those obtainable by the administration of the haematopoietic factor alone.

The subject of the present disclosure is therefore represented by a formulation containing as "active agents" defibrotide in combination with at least one haematopoietic factor having the capacity to mobilise haematopoietic progenitors, preferably G-CSF. In one embodiment, this formulation is constituted by an injectable aqueous solution; alternatively, the formulation could be constituted by two different solutions, one containing defibrotide and the other containing the haematopoietic factor having the capacity to mobilise haematopoietic progenitors. One formulation used in the technique is therefore shaped as a combined preparation for simultaneous, separate or sequential use of the aforementioned active principles in order to increase the amount of stem cells and/or haematopoietic progenitors in circulation in the peripherial blood of a mammal.

A second subject of the innovation is represented by the use of defibrotide, in combination with at least one haematopoietic factor having the capacity to mobilise haematopoietic progenitors, for the preparation of formulations capable of increasing the amount of stem cells and/or haematopoietic progenitors in circulation in the peripheral blood of a mammal, preferably a human being.

Finally, a further subject of the innovation is represented by a method of increasing the amount of stem cells and/or haematopoietic progenitors in circulation in the peripheral blood of a mammal, characterised in that defibrotide is administered to the mammal in combination or in temporal proximity with at least one haematopoietic factor having the capacity to mobilise haematopoietic progenitors. The haematopoietic factor used to conduct the experiments which led to the present innovation is G-CSF; however, it is not to be excluded that similar results may be obtained with haematopoietic factors other than G-CSF but nevertheless having the capacity to mobilise haematopoietic progenitors, such as, for example, the growth factor of granulocyte and macrophage colonies (GM-CSF), "Flt3 ligand" (FL), "stem cell factor" (SCP), thrombopoietin (TPO), interleukin 8 (IL-8), and others which will be clear to persons skilled in the art.

The defibrotide used in combination with G-CSF in this first experimental stage was the defibrotide currently marketed by Crinos Spa under the mark Prociclide™ and produced in accordance with the process described in U.S. Pat. No. 4,985,552 and U.S. Pat. No. 5,223,609. As regards the methods of administering the two active ingredients, they are not limiting for the purposes of the invention. That is to say, defibrotide and haematopoietic factor having the capacity to mobilise haematopoietic progenitors can be administered to mammals (and in particular to human beings) in accordance with the methods and the posologies known in the art; generally, they are administered orally, intramuscularly, intraperitoneally, subcutaneously or intravenously, the last-mentioned route being the preferred one.

The two active ingredients can also be administered simultaneously or in succession. That is to say, in the first case, they are administered by means of a single formulation which contains both of the active ingredients and to which the usual excipients and/or coadjuvants known in the art have optionally been added; alternatively, the two active ingredients may be administered sequentially, namely, by means of two different formulations, one containing the haematopoietic factor having the capacity to mobilise haematopoietic progenitors, preferably G-CSF, and the other containing the defibrotide.

Generally, G-CSF will be administered subcutaneously, at a dosage of 5 to 24 μg/kg whereas DEF will be administered by continuous infusion at a dosage of 5 to 15 mg/kg/hr for 2-7 days. As will be appreciated from the accompanying Examples, which are to be regarded purely as non-limiting illustrations of the invention, the combined administration of G-CSF and defibrotide to mice, as the most common experimental mammal model, and to monkeys, permits the attainment of levels of mobilisation much higher than those obtainable by the administration of G-CSF alone, with cleat advantages for all those therapeutic sectors for which a high level of mobilization is desirable.

Example 1

This experiment was carried out to evaluate the effect of the administration of G-CSF and/or defibrotide (DEF) on the amount of white blood cells (WBC) present in murine blood. BALB/c mice from 6 to 8 weeks old and having a body weight of from 20 to 25 g were subjected to intraperitoneal (IP) injections of G-CSF (5 μg/mouse/day), DEF (1 mg/mouse/day), or a combination of G-CSF (5 μg/mouse/day) and increasing doses of DEF (1, 10, 15 mg/mouse/day). A saline solution, buffered to 0.1%, of marine serum albumin (PBS/MSA) was administered by IP injection to the control mice which had not received G-CSF and/or DEF. The mice were treated for 5 days and sacrificed after 3 or 5 days of treatment, or 3 days after therapy had ceased. The results of this experiment are given in FIG. 1. The following symbols were used to represent each group of mice: G-CSF (■) (n=24), DEF 1 (○) (n=3), G-CSF+DEF 1 (♦) (n=13), G-CSF+DEF 10 (▲) (n=6), G-CSF+DEF 15 (●) (n=23). The mean white blood cell count in PBS/MSA in the control mice was $2.87\pm0.2\times10^6$/ml of blood; the data ate expressed as mean± standard error of the mean (SEM).

Example 2

Figure 2:
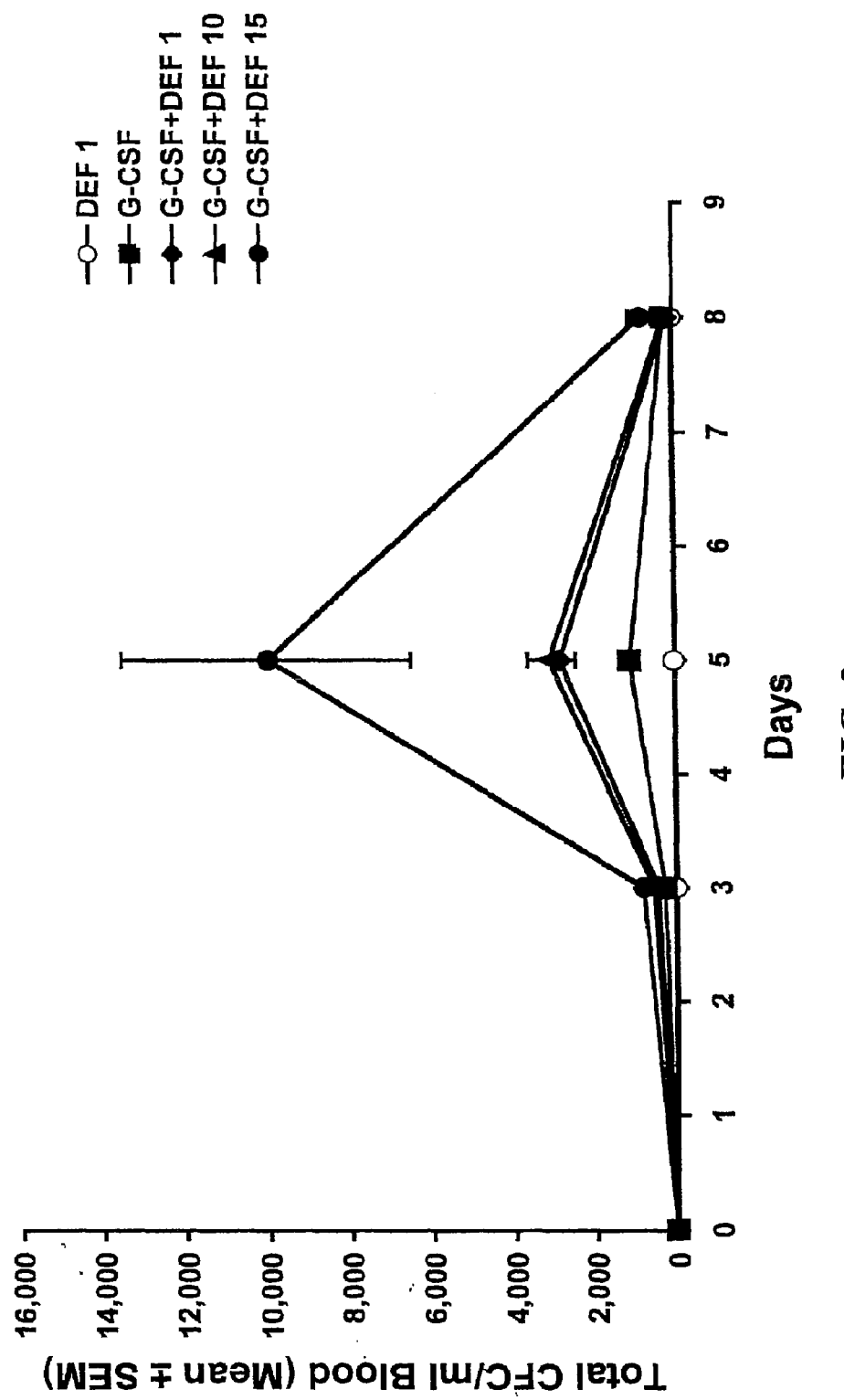
FIG. 2 shows the mobilization kinetics of the total number of colonies forming cells (CFCs) per milliliter of blood in the mice of Example 1 over days.

Mobilization kinetics of the cells forming the total colonies (CFC) per milliliter of blood of the mice of Example 1. The mean CFC count in PBS/MSA in the control mice was 39±12 per ml of blood; the data are given in FIG. 2 and are expressed as mean± SEM derived from duplicated cultures on samples from each animal at each point in time.

Example 3

Figure 3:
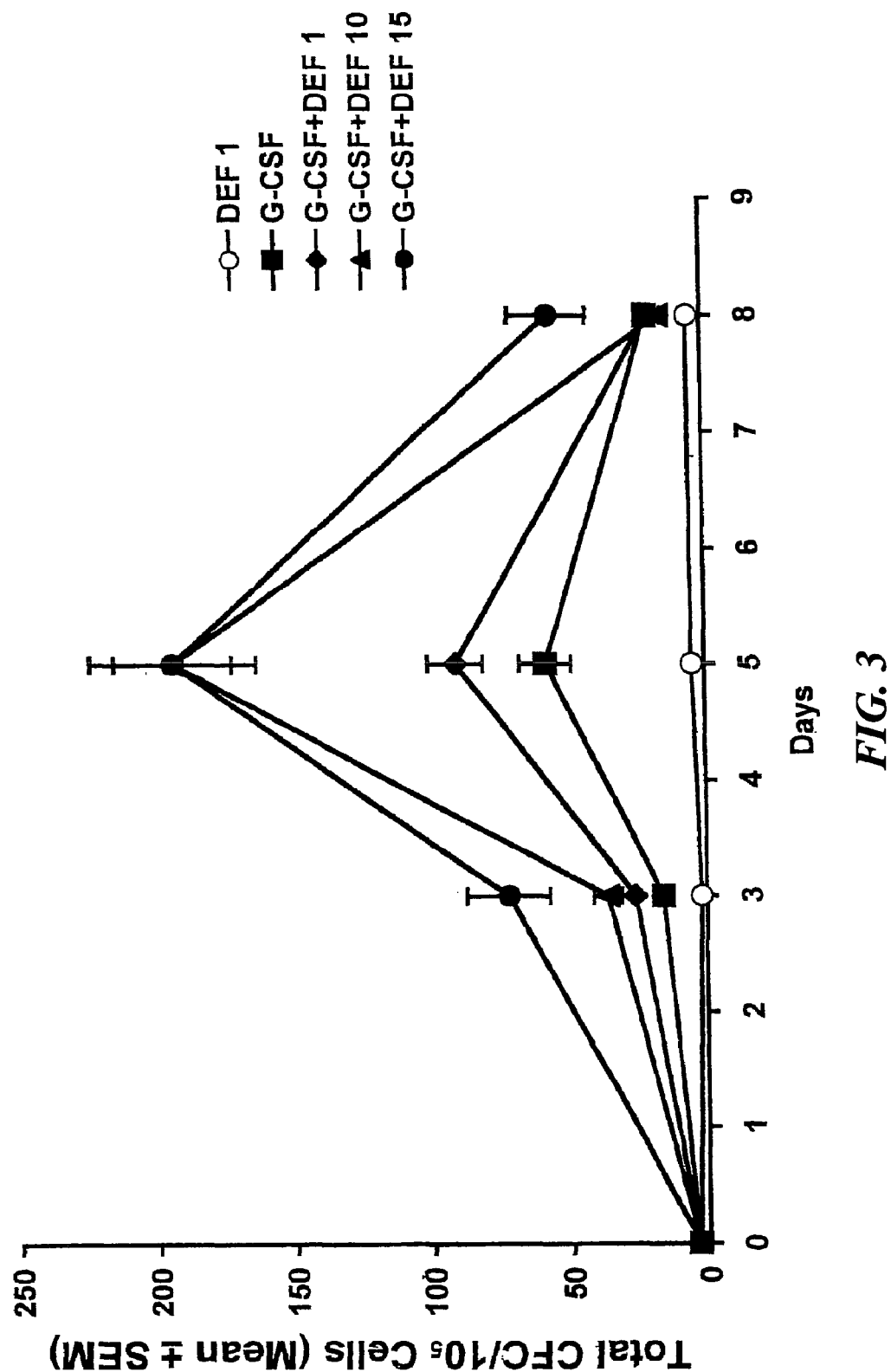
FIG. 3 shows the total number of CFCs per $10^5$ buffy-coat cells of peripheral blood in the mice of Example 1 over days.

Changes in the frequency of the total CFCs (CFU-GM+ BFU-E+CFU-Mix HPP-CFC) per $10^5$ buffy-coat cells of peripheral blood in the mice mentioned in Example 1. The mean CFC count in PBS/MSA in the control mice was 3.5±1; the data are given in FIG. 3 and are expressed as mean± SEM derived from duplicated cultures on samples from each animal at each point in time.

Example 4

Figure 4:
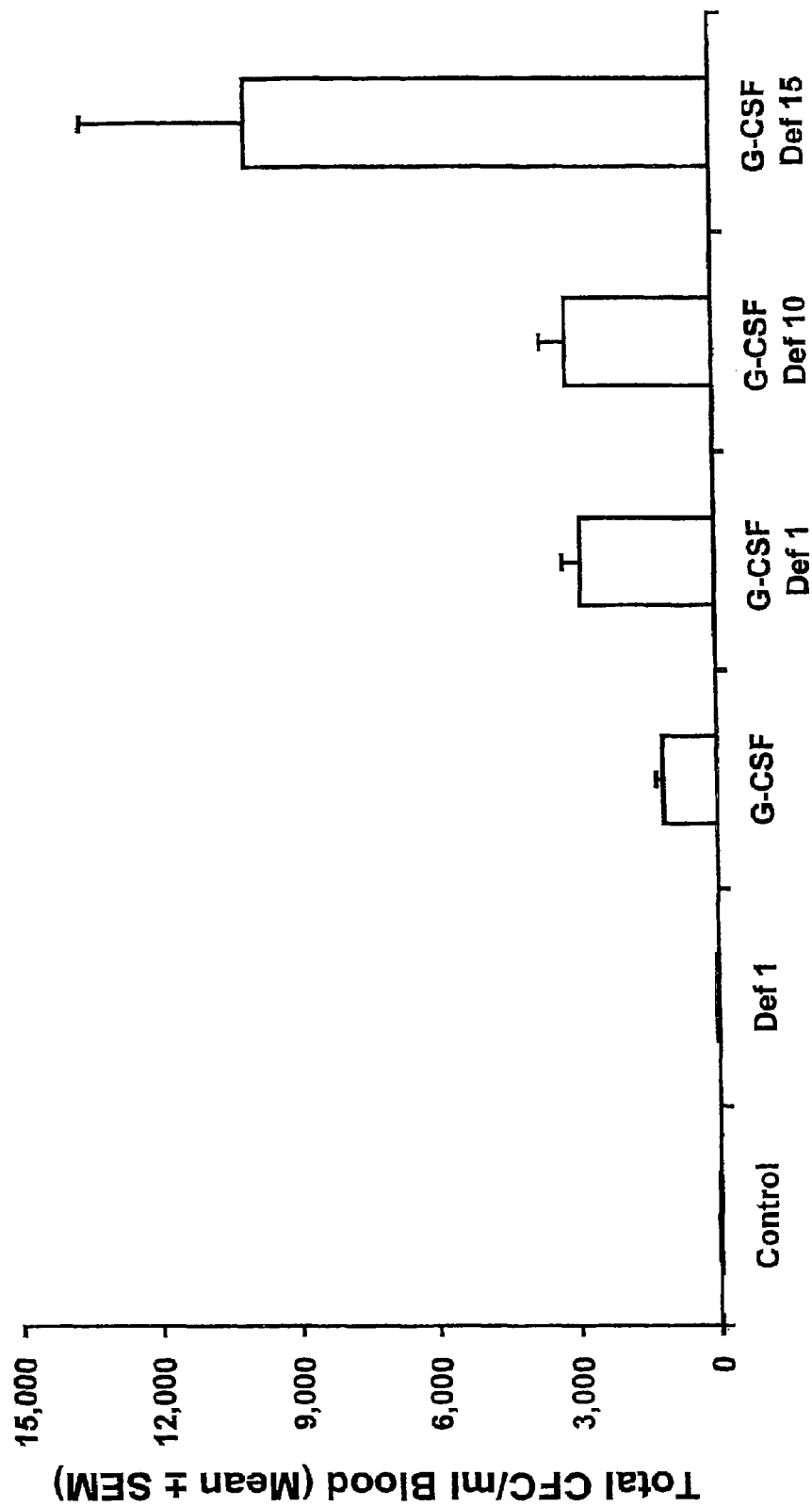
FIG. 4 shows the total number of CFCs per milliliter of blood in the mice of Example 1 after 5 days' treatment.

Total CFCs (CFU-GM+BFU-E+CFU-Mix+HPP-CFC) per milliliter of blood after 5 days' treatment of the mice of Example 1; the data are given in FIG. 4 and are expressed as mean± SEM derived from duplicated cultures on samples from each animal.

Example 5

Figure 5:
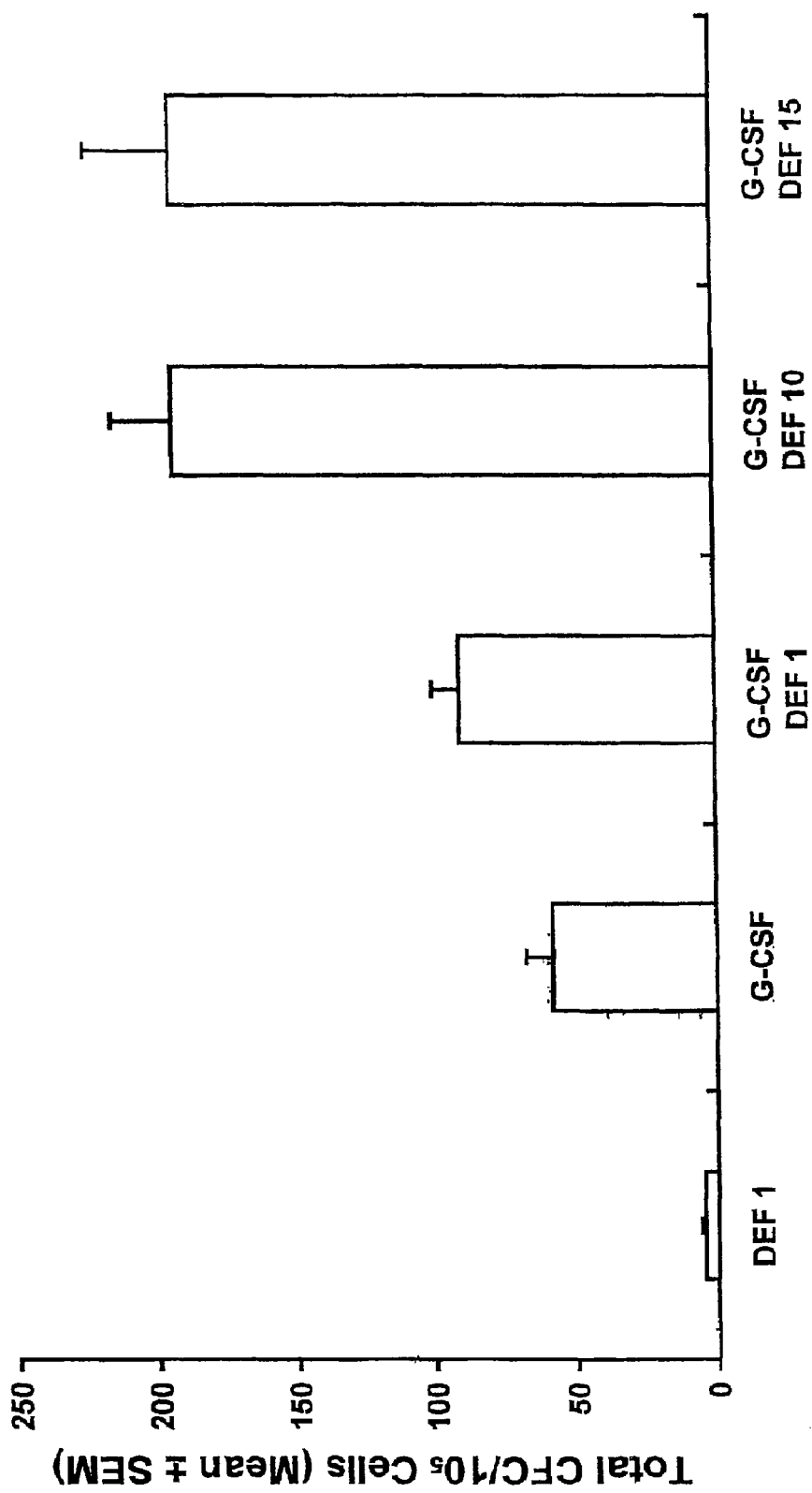
FIG. 5 shows the total number of CFCs per $10^5$ buffy-coat cells of peripheral blood in the mice of Example 1 after 5 days' treatment.

Frequency of the total CFCs (CPU-GM+BFU-E+CFU-Mix+HPP-CFC) for $10^5$ buffy-coat cells of peripheral blood in the mice mentioned in Example 1; the data are given in FIG. 5 and are expressed as mean± SEM derived from duplicated cultures on samples from each animal.

Example 6

Figure 6:
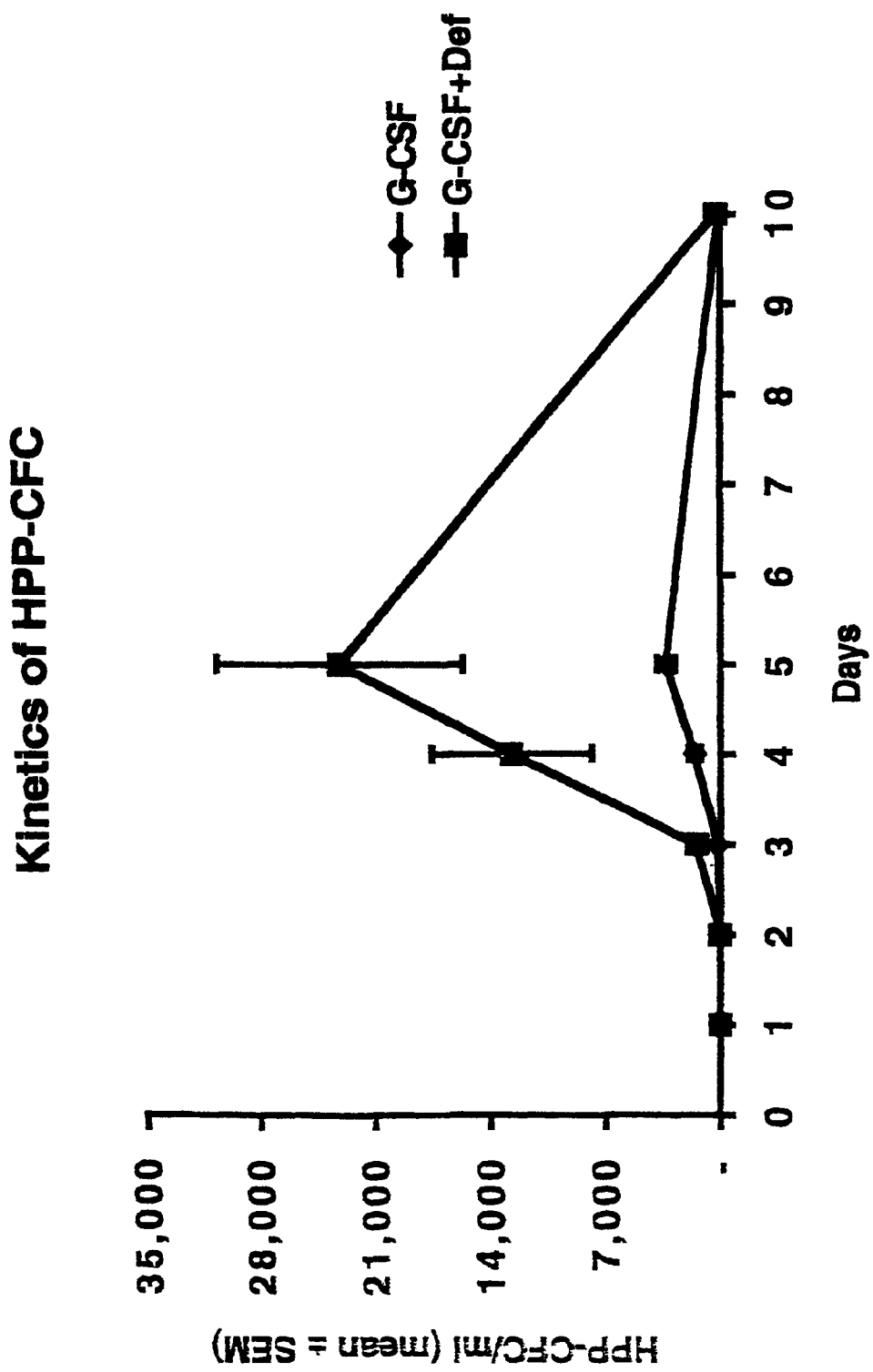
FIG. 6 shows the effect of the administration of G-CSF alone or with DEF on the amount of haematopoietic progenitors/stem cells (High-Proliferative Potentia-Colony Stimulating Cells, or HPP-CFC) in circulation in the peripheral blood of monkeys over days.

This experiment was carried out to evaluate the effect of the administration of G-CSF alone or with DEF on the amount of haematopoietic progenitors/stem cells (High-Proliferative Potentia-Colony Stimulating Cells, or HPP-CFC) in circulation in the peripheral blood of monkeys. The study was carried out in rhesus monkeys (*Macaca Mulatta*) of 4-6 years in good health and which showed normal values for hematology and clinical chemistry. The G-CSF was dosed subcutaneously, 100 µg/kg, for 5 days for two cycles; DEF was dosed 15 mg/kg/hr by a continuous infusion system for 5 days at the second cycle. The animals were anaesthetised for bleeding, administration of G-CSF and changing the drug-bag. The results of this experiment are given in FIG. 6, from which it can be appreciated that the combined administration of G-CSF and defibrotide enables an HPP-CFC mobilization in monkeys which is about 8 times higher than that obtainable by the administration of G-CSF alone.

CONCLUSIONS

As will be readily appreciated from the data given in FIG. 1, the combined administration of G-CSF and defibrotide produces a substantial increase in the amount of white blood cells in circulation in murine blood. It should, in particular, be noted that the administration of defibrotide alone does not have a positive influence on the amount of white blood cells in circulation; the combination of G-CSF and defibrotide therefore produces a surprising dose-dependent effect of increasing the number of white blood cells, which is not merely the sum of two effects which are independent of one another.

FIGS. 2 to 5 clearly indicate that the combined administration of G-CSF and defibrotide enables levels of mobilization to be obtained in mice that are from 10 to 100 times higher than those obtainable by the administration of G-CSF alone. Finally, FIG. 6 confirms that the combined administration of G-CSF and defibrotide enables a stem cell (HPP-CFC) mobilization in monkeys which is about 8 times higher than that obtainable by the administration of G-CSF alone.

The combined effect of the two active ingredients is dose-dependent because the levels of mobilization increase proportionally with the amount of defibrotide administered; the highest mobilisation peak is reached in all cases on approximately the fifth day from administration.

What is claimed is:

1. A method for increasing the amount of stem cells and/or haematopoietic progenitors in the peripheral blood of a mammal, comprising:
    administering defibrotide as described in Chemical Abstract Registry No. 83712-60-1 and at least one haematopoietic factor having the capacity to mobilize haematopoietic progenitors to a mammal.

2. The method according to claim 1, wherein said defibrotide and said haematopoietic factor are administered simultaneously.

3. The method according to claim 1, wherein said defibrotide and said haematopoietic factor are administered separately.

4. The method according to claim 1, wherein said defibrotide and said haematopoietic factor are administered sequentially.

5. The method according to claim 1, wherein the haematopoietic factor is G-CSF, GM-CSF, Flt3 ligand, stem cell factor, thrombopoietin, or interleukin 8.

6. The method according to claim 5, wherein the haematopoietic factor is G-CSF.

7. The method according to claim 1, wherein said defibrotide and said haematopoietic factor are independently administered intravenously, orally, intramuscularly, intraperitoneally, or subcutaneously.

8. The method according to claim 1, wherein said defibrotide is administered by continuous infusion.

9. The method according to claim 8, wherein said defibrotide is administered at a dosage of 5-15 mg/kg/hour for 2-7 days.

10. The method according to claim 1, wherein said haematopoietic factor is administered subcutaneously.

11. The method according to claim 10, wherein said haematopoietic factor is administered at a dosage of 5-24 µg/kg.

12. The method according to claim 1, wherein the defibrotide is in an aqueous solution.

13. The method according to claim 1, wherein the haematopoietic factor is in an aqueous solution.

14. The method according to claim 1, wherein the defibrotide is in a form of an alkali metal salt.

15. The method according to claim 14, wherein said alkali metal is sodium.

16. The method according to claim 1, wherein the mammal is a human.

* * * * *